United States Patent [19]
Johnson et al.

[11] Patent Number: 6,136,029
[45] Date of Patent: *Oct. 24, 2000

[54] BONE SUBSTITUTE MATERIALS

[75] Inventors: Wesley D. Johnson, Menomonie, Wis.; James R. Johnson, Boca Raton, Fla.; Jeffrey G. Marx, Menomonie, Wis.

[73] Assignee: Phillips-Origen Ceramic Technology, LLC, Prescott, Wis.

[*] Notice: This patent issued on a continued prosecution application filed under 37 CFR 1.53(d), and is subject to the twenty year patent term provisions of 35 U.S.C. 154(a)(2).

[21] Appl. No.: 08/942,557

[22] Filed: Oct. 1, 1997

[51] Int. Cl.⁷ ..................................................... A61F 2/28
[52] U.S. Cl. .............................. 623/16; 623/11; 427/2.27
[58] Field of Search ............................ 623/11, 16, 16 D, 623/16 E, 66; 427/2.27

[56] References Cited

U.S. PATENT DOCUMENTS

| | | |
|---|---|---|
| 4,000,525 | 1/1977 | Klawitter et al. . |
| 4,237,559 | 12/1980 | Borom . |
| 4,343,704 | 8/1982 | Brockmeyer . |
| 4,599,085 | 7/1986 | Riess et al. . |
| 4,626,392 | 12/1986 | Kondo et al. . |

(List continued on next page.)

FOREIGN PATENT DOCUMENTS

| | | |
|---|---|---|
| 0299342 | 1/1989 | European Pat. Off. . |
| 0585978 | 3/1994 | European Pat. Off. . |
| 0714666 | 6/1996 | European Pat. Off. . |
| 19610715 | 6/1997 | Germany . |
| 4-15062 | 1/1992 | Japan . |
| WO 95 28973 | 11/1995 | WIPO . |

OTHER PUBLICATIONS

Aksaci, D., et al., "Porous Fluorapatite/Spinel Osteoceramic For Bone Bridges", Phosphorus: Studies in Inorganic Chemistry, vol. 6, 1985, pp. 283–301.

McGee, Thomas D., et al., "General Requirements for a Successful Orthopedic Implant", pp. 69–82.

Ito, Kuniomi, et al., "Osteogenic Activity of Synthetic Hydroxylapatite With Controlled Texture–on the Relationship of Osteogenic Quantity . . . ", CRC Handbook of Bioactive Ceramics, vol. II, pp. 39–44.

Johnson, Kenneth D., et al., "Porous Ceramics as Bone Graft Substitutes in Long Bone Defects . . . ", J. Orthop. Rev., vol. 14, No. 3, 1996, pp. 351–369.

"Bone Grafts and Bone Substitutes", Orthopedic Network News, vol. 6, No. 4, Oct. 1995, pp. 7–9.

(List continued on next page.)

*Primary Examiner*—David H. Willse
*Assistant Examiner*—Dinh X. Nguyen
*Attorney, Agent, or Firm*—Fredrikson & Byron, P.A.

[57] ABSTRACT

A strong, porous article useful as a bone substitute material and having an outer surface defining a shape having a bulk volume and having open interconnecting interstices extending throughout said volume and opening through said surface. The article comprises a continuous strong framework structure having interstices which interconnect throughout the bulk volume and a second continuous material occupying at least a portion of the same bulk volume as the framework structure. The second material comprises an osteoinductive and/or osteoconductive composition. This composition may be present in one of several forms. One of these is as a coating on the surface of the framework structure. A second form is in the form of a composite, intimately mixed with the framework material within the framework struts. The third form is as a porous mass within the interstices of the framework structure, having pores which are interconnecting with themselves, and with the interstices of the framework structure. Desirably, the porous osteoinductive or osteoconductive composition extends throughout said bulk volume. In a preferred embodiment, the framework structure is formed of a ceramic material. In a further embodiment, the framework structure may be further structurally reinforced with a dense material component integrally affixed thereto.

21 Claims, 3 Drawing Sheets

U.S. PATENT DOCUMENTS

| | | |
|---|---|---|
| 4,722,870 | 2/1988 | White . |
| 4,957,509 | 9/1990 | Tamari et al. . |
| 4,976,736 | 12/1990 | White et al. ............................. 623/16 |
| 4,983,182 | 1/1991 | Kijima et al. . |
| 5,001,169 | 3/1991 | Nathan et al. . |
| 5,007,930 | 4/1991 | Dorman et al. . |
| 5,037,438 | 8/1991 | Davidson ................................. 623/18 |
| 5,084,051 | 1/1992 | Tormala et al. . |
| 5,152,791 | 10/1992 | Hakamatsuka et al. . |
| 5,185,177 | 2/1993 | Kijima et al. ............................... 427/2 |
| 5,192,325 | 3/1993 | Kijima et al. ............................. 623/16 |
| 5,205,921 | 4/1993 | Shirkanzadeh ....................... 623/16 X |
| 5,231,169 | 7/1993 | Constantz et al. . |
| 5,282,861 | 2/1994 | Kaplan ..................................... 623/16 |
| 5,356,436 | 10/1994 | Nonami et al. .......................... 623/16 |
| 5,366,508 | 11/1994 | Brekke ..................................... 623/16 |
| 5,458,643 | 10/1995 | Oka et al. ................................ 623/18 |
| 5,464,440 | 11/1995 | Johansson ................................ 623/16 |
| 5,522,894 | 6/1996 | Klaus . |
| 5,549,123 | 8/1996 | Okayama et al. ...................... 128/898 |
| 5,549,685 | 8/1996 | Hayes ...................................... 623/20 |
| 5,626,861 | 5/1997 | Laurencin et al. . |
| 5,716,414 | 2/1998 | Caldarise ................................. 623/16 |
| 5,725,813 | 3/1998 | Nies ..................................... 623/16 X |
| 5,783,248 | 7/1998 | Ruey et al. . |

OTHER PUBLICATIONS

Constantz, Brent R., et al., "Skeletal Repair by in Situ Formation of the Mineral Phase of Bone", Science, vol. 267, Mar. 24, 1995, pp. 1796–1799.

Chaki, T.K., et al, "Strengthening Behavior of Hydroxyapatite–Silver Composite", Bioceramics: Materials and Applications, pp. 235–244.

Damien, C., et al., "Bone Graft and Bone Graft Substitutes: A Review of Current Technology and Applications", J. App. Biomat., vol. 2, 1991, pp. 187–208.

Ioku, Koji, et al., "Dense/porous Layered Apatite Ceramics Prepared by HIP Post–sintering", J. Mat. Science, 1989, pp. 1203–1204.

Wu, Jenn–Ming, et al., "Sintering of Hydroxylapatite–zirconia Composite Materials", J. Mat. Science, 1988, pp. 3771–3777.

Li, J., et al., "High–strength biofunctional zirconia: mechanical properties and static fatigue behavior of zirconia–apatite composites", J. Bio. Sci. Mat., 1993, pp. 50–54.

Suda, Akio, et al., "Biocompatibility of Zirconia Dispersed Hydroxyaptite Ceramics", J. Jap. Orthop. Assoc., vol. 64, pp. 249–258.

Takaoka, Kunio, et al., "Ectopic Bone Induction on and in Porous Hydroxyapatite Combined with Collagen and Bone Morphogenetic Protein", Clinical Orthopedics, No. 234, Sep. 1988, pp. 250–254.

Mattioli–Belmonte, et al., "Osteoinduction in the Presence of Chitosan–Coated Porous Hydroxyapatite", J. Bio. Comp. Poly., vol. 10, Jul. 1995, pp. 249–257.

Wan, Andrew, et al., "Hydroxyapatite Modified Chitin as Potential Hard Tissue Substitute Material", J. Bio. Mat. Res. [38] 3 (1997), pp. 235–241.

Zhang, Qi–Qing, "Porous Hydroxyapatite Reinforced with Collagen Protein", Marcel Dekker, Inc., 1996, pp. 693–702.

Gao, T., et al., "Enhanced healing of segmental tibial defects in sheep by a composite bone substitute composed of tricalcium phosphate cylinder, bone . . . ", J. Bio. Mat. Res., vol. 32, (1996) pp. 505–512.

Verheyen, et al., "Hydroxylapatite/poly (L–lactide) composites: An animal study on push–out strengths and interface histology", J. Bio. Mat. Res., vol. 27, (1993), pp. 433–444.

TenHuisen, K., et al., "Formation and properties of a synthetic bone composite: Hydroxyapatite–collagen", J. Bio. Mat. Res., vol. 29, (1995), pp. 803–810.

Muller–Mai, C., et al., "Nanoapatite and organoapatite implants in bone: Histology and ultrastructure of the interface", J. Bio. Mat. Res., vol. 29, (1995) pp. 9–18.

Tian, Y., "A Novel Chondrocyte–Seeded Hydroxyapatite–Collagen Scaffold for Cartilage Repair", Fifth World Biomaterials Congress, May 29–Jun. 2, 1996.

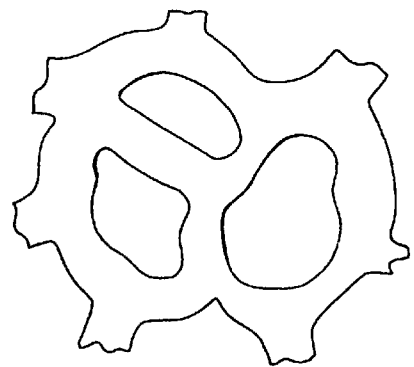
Fig. 1
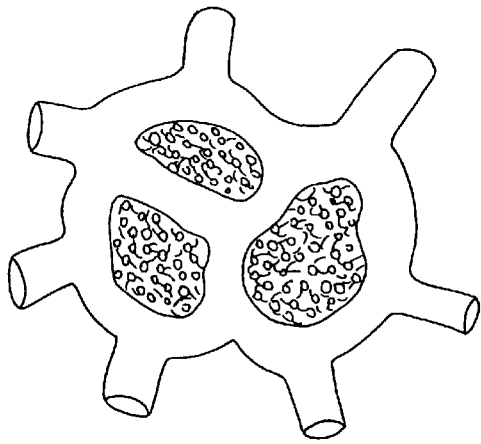
Fig. 2
Fig. 3
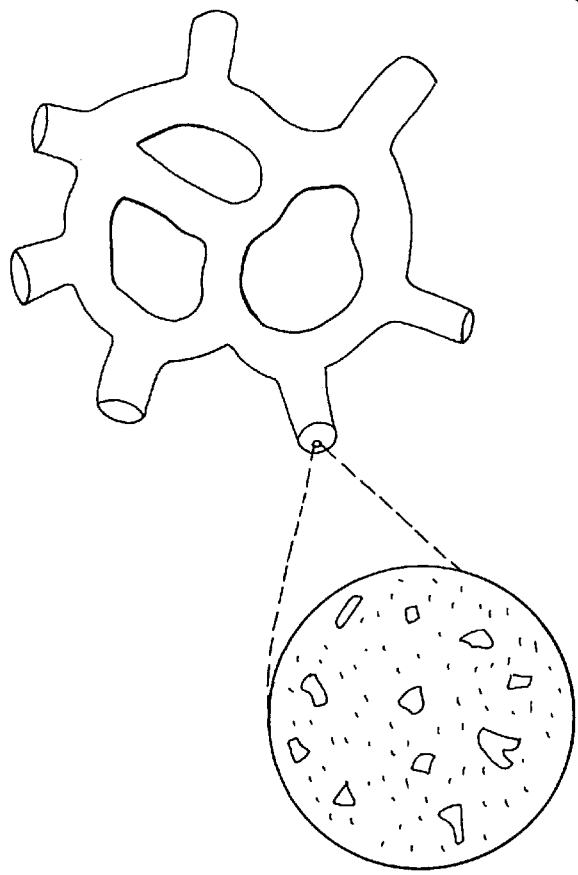

BONE SUBSTITUTE MATERIALS

FIELD OF THE INVENTION

The present invention relates in general to bone substitute materials, and particularly to porous materials capable of supporting or encouraging bone ingrowth into its pores.

BACKGROUND OF THE INVENTION

In the case of fracture or other injury to bone, proper bone healing and subsequent favorable bone remodeling is highly dependent on maintaining stability between bone fragments and, in the case of decalcified bone, on maintaining physiologic strain levels. External structural support can be gained using external braces, casts and the like. Internal structural support commonly is supplied by internal fixation devices such as bone plates, screws, intramedullar rods, etc., some of which may need to be surgically removed at a later time and all of which may prove to be burdensome and traumatic to a patient.

There is thus a need for a product that is a bone substitute product that is a bone graft material and that also provides structural support. This is especially so in the replacement or repair of long bones of the lower extremities and for use in spinal fusion techniques. Trauma, osteoporosis, severe osteo arthritis or rheumatoid arthritis, joint replacement, and bone cancers may call for treatment involving the use of structural bone substitute materials.

A successful bone graft requires an osteoconductive matrix providing a scaffold for bone ingrowth, osteoinductive factors providing chemical agents that induce bone regeneration and repair, osteogenic cells providing the basic building blocks for bone regeneration by their ability to differentiate into osteoblasts and osteoclasts, and structural integrity provided to the graft site suitable for the loads to be carried by the graft.

Current bone graft materials include autografts (the use of bone from the patient), allografts (the use of cadaver bone), and a variety of artificial or synthetic bone substitute materials. Autografts grafts are comprised of cancellous bone and/or cortical bone. Cancellous bone grafts provide virtually no structural integrity. Bone strength increases as the graft incorporates and new bone is laid down. For cortical bone, the graft initially provides some structural strength. However, as the graft is incorporated by the host bone, nonviable bone is removed by resorption significantly reducing the strength of the graft. The use of autograft bone may result in severe patient pain at the harvest site, and there is of course a limit to the amount of such bone that can be harvested from the patient. Allografts are similar to autografts in that they are comprised of cancellous and/or cortical bone with greater quantities and sizes being available. Sterilization techniques for allografts may compromise the structural and biochemical properties of the graft. The use of autograft bone bears at least some risk of transfer of disease and the risk that the graft may not be well incorporated.

For structural bone repair materials to be conveniently used, they must be capable of being formed into complex shapes that are designed to fit the contours of the repair site. An accurately contoured graft will enhance the integration of natural bone and provide better load carrying capability. Intimate, load carrying contact often is required between the natural bone and the bone substitute material to promote bone remodeling and regeneration leading to incorporation of the graft by host bone.

A general overview of orthopedic implantable materials is given in Damien, Christopher J., and Parsons, Russell J., "Bone Graft and Bone Graft Substitutes: A Review of Current Technology and Applications," Journal of Applied Biomaterials. Vol. 2. pp. 187–208 (1991).

A variety of materials have been proposed for use as bone substitute materials, ranging from shaped porous metal objects suitable for defect filling around knee and hip joint replacements on the one hand to shaped ceramic materials on the other. Ceramic materials by and large have been formed through a sintering process in which a powder of a ceramic material such as zirconia is compressed to a desired shape in a mold and is then heated to sintering temperatures. The porosity of the resulting material is commonly quite low. Materials employing calcium phosphates (for example: fluorapatite, hydroxyapatite, and tricalcium phosphate) can also be sintered in this manner, the calcium phosphate having the capacity for acting as a substrate for bone growth (osteoconductivity).

It has been suggested to mix ceramic powders such as zirconia and hydroxyapatite, and fluorapatite and spinel, and then compress the mixture in a mold and either sinter or hot isostatically press to produce a somewhat porous ceramic of zirconia having pores at least partially filled with hydroxyapatite. Reference is made to Tamari et al., U.S. Pat. No. 4,957,509, and also Aksaci, D. et al., Porous Fluorapatite/spinel Osteoceramic for Bone Bridges, Ceramic Transactions, Vol. 48 p. 283 (1995). It has also been suggested to use ceramic articles having both high porosity and low porosity portions, and reference is made here to Hakamatsuka et al., U.S. Pat. No. 5,152,791, Johansson, U.S. Pat. No. 5,464,440 and Borom, U.S. Pat. No. 4,237,559. See also Klawitter et al. U.S. Pat. No. 4,000,525. The latter reference refers to the use of an $Al_2O_3$ slip that is foamed into a sponge, followed by firing.

By and large, metal or ceramic materials that have been proposed for bone substitutes have been of low porosity. The art contains examples of substantially dense metals and ceramics with a semi-porous surface which is filled or coated with a calcium phosphate based material. The resulting structure has a dense metal or ceramic core and a surface which is a composite of the core material and a calcium phosphate, or a surface which is essentially a calcium phosphate. The bone substitute materials of this type commonly are heavy and dense, and often are significantly stiffer in structure than bone. Reference here is made to U.S. Pat. Nos. 5,306,673 (Hermansson et al.), 4,599,085 (Riess et al.), 4,626,392 (Kondo et al.), and 4,967,509 (Tamari et al.).

SUMMARY OF THE INVENTION

The present invention provides a strong, open-celled article that is useful as a bone substitute material and that is highly porous so as to accommodate bone ingrowth, is of low density, and which includes a material that fosters bone ingrowth.

In one embodiment, the invention relates to an open-celled article or reticulum having an outer surface defining a bulk volume and having interconnecting openings extending throughout the volume and opening through the outer surface. The article comprises a continuous strong supportive framework, preferably ceramic, having struts defining a plurality of interconnecting interstices throughout the bulk volume, and a porous osteoconductive composition carried by said supporting framework and exposed to the interconnected openings. The porous osteoconductive composition occupies at least a portion of the same bulk volume as the framework component. Desirably, the articles of the invention have void volumes that are in the range of 20% to 90% and preferably at least 50%. Further, the mean size of the openings of the supportive framework component desirably are at least 50 μm and preferably are in the range of 200 μm to 600 μm In a preferred embodiment, the supportive framework and the osteoconductive composition each are continuous three dimensional structures that exhibit 3,3 connectivity and occupy at least a portion and preferably the entirety of the same bulk volume, each continuous structure having interconnected openings that interconnect with the openings of the other. The osteoconductive composition may be carried within the openings of the supportive framework preferably as a continuous phase on the surface of the struts, and pores of the osteoconductive composition communicate with but may or may not be coextensive with the interstices of the supportive framework.

In yet another embodiment, the struts are comprised of a mixture or composite which contains the supportive material as well as osteoconductive material, the support material providing strength to the article and the osteoconductive material being carried at least partially on the surface of the interstices so as to be exposed to the interconnected openings to provide an osteoconductive environment favoring bone growth.

In another embodiment, the invention comprises an open celled article of any of the several types described above and including a second substantially dense continuous material component attached to a surface of the bulk volume of the first material, the second component having a porosity not greater than 10% of its bulk volume. This substantially dense phase may be either a ceramic, a polymer, a metal, or a composite material, and the product may find utility as a hip stem or tibial tray of an implantable prosthesis.

DESCRIPTION OF THE DRAWING

FIG. 1 is a schematic drawing of a ceramic based article of the invention illustrating the continuous open nature of the support structure;

FIG. 2 is a schematic drawing of a ceramic based article of the invention illustrating an osteoconductive material foamed within the interstices of the supportive framework support;

FIG. 3 is a drawing of an embodiment of the invention in which the struts are a composite containing both support and osteoconductive materials;

DETAILED DESCRIPTION OF THE PREFERRED EMBODIMENT

Figure 4:
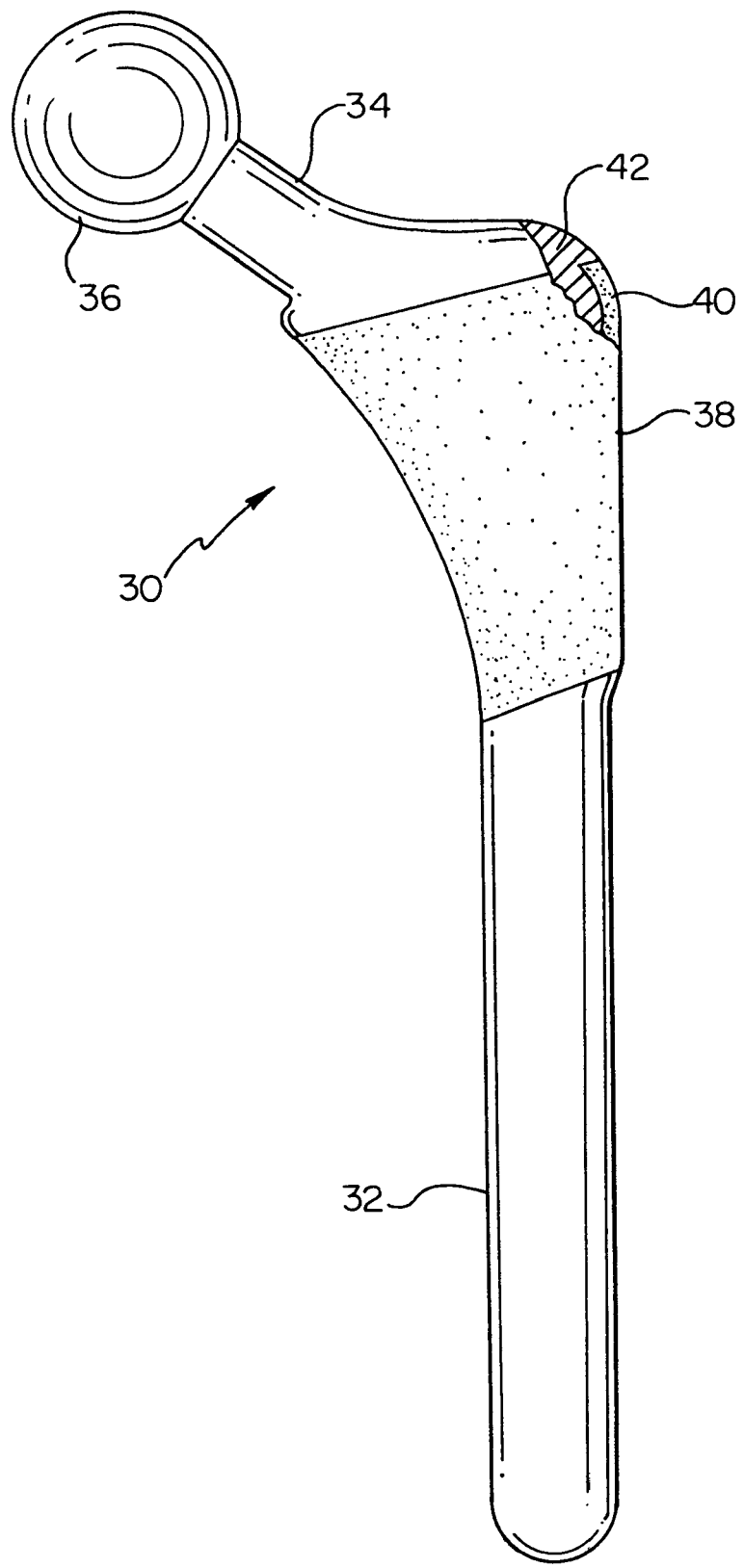
FIG. 4 is a broken away view of a femoral prosthesis utilizing an embodiment of the invention.

In preparing articles of the invention, it is preferred to begin with the formation of a hard, strong, open framework having interstices in the size range of about 50 μm to about 1000 μm and preferably from about 200 μm to about 600 μm and having void volumes of at least about 30%, preferably at least about 50% and most preferably at least about 70%. The material of the framework may comprise any strong, hard, biologically-compatible material such as ceramic materials, metals and composites such as zirconia/hydroxyapatite or zirconia toughened alumina. Preferably, the framework component is of a ceramic material, zirconia and alumina being preferred.

In one preferred method, a slip of ceramic material is made by combining a ceramic powder such as zirconia with an organic binder and water to form a dispersion. The strut surfaces of an organic reticulated foam such as one of the various commercially available foams made of polyurethane, polyester, polyether, or the like are wetted and coated with the ceramic slip. The reticulated material may be immersed in the slip, and then removed and drained to remove excess slip. If desired, further excess slip can be removed by any of a variety of methods including passing the material between a pair of closely spaced rollers or by impacting the material with a jet of air. Varying the slip concentration, viscosity, and surface tension provides control over the amount of slip that is retained on the foam strut surfaces. Wetting agents and viscosity control agents also may be used for this purpose. A wide variety of reticulated, open cell materials can be employed, including natural and synthetic sponge materials and woven and non-woven materials, it being necessary in this embodiment only that the open cell material enables ceramic slip material to penetrate substantially fully through the openings in the structure.

Once the reticular struts are coated with slip, the slip solvent is removed by drying, accompanied desirably by mild heating, and the structure is then raised to sintering temperatures at which the ceramic particles at least partially sinter to one another to form a rigid, light framework structure that mimics the configuration of the reticular struts. Before reaching sintering temperatures, the slip-treated sponge desirably is held at a temperature at which the organic material pyrolizes or burns away, leaving behind an incompletely sintered ceramic framework structure which then is raised to the appropriate sintering temperature.

Pyrolizing or oxidizing temperatures for most organics are in the range of about 200° C. to about 600° C. and sintering temperatures for most ceramics of relevance to this invention are in the range of about 1100° C. to about 1600° C. Zirconia and alumina or composites based on zirconia and alumina are the preferred ceramic materials for the structural elements. Examples of ceramic materials for the osteoconductive portion include calcium phosphates (e.g., hydroxyapatite, fluorapatite, and tricalcium phosphate and mixtures thereof), bioactive glasses, osteoconductive cements, and compositions containing calcium sulfate or calcium carbonate.

Metals which can be used to form the hard, strong, continuous framework component include titanium, stainless steels, cobalt/chrome alloys, tantalum, titanium-nickel alloys such as Nitinol and other superelastic metal alloys. Reference is made to Itin, et al., "Mechanical Properties and Shape Memory of Porous Nitinol," Materials Characterization [32] pp. 179–187 (1994); Bobyn, et al., "Bone Ingrowth Kinetics and Interface Mechanics of a Porous Tantalum Implant Material," Transactions of the 43rd Annual Meeting, Orthopaedic Research Society, p. 758, Feb. 9–13, 1997 San Francisco, Calif.; and to Pederson, et al., "Finite Element Characterization of a Porous Tantalum Material for Treatment of Avascular Necrosis," Transactions of the 43rd Annual Meeting, Orthopaedic Research Society, p. 598 Feb. 9–13, 1997. San Francisco, Calif., the teachings of all of which are incorporated by reference.

Metals can be formed into a hard, strong, continuous supportive frameworks by a variety of manufacturing procedures including combustion synthesis, plating onto a "foam" substrate, chemical vapor deposition (see U.S. Pat. No. 5,282,861), lost mold techniques (see U.S. Pat. No. 3,616,841), foaming molten metal (see U.S. Pat. Nos. 5,281,251, 3,816,952 and 3,790,365) and replication of reticulated polymeric foams with a slurry of metal powder as described for ceramic powders.

The osteoconductive and osteoinductive materials that are appropriate for use in the present invention are biologically acceptable and include such osteoconductive materials as collagen and the various forms of calcium phosphates including hydroxyapatite; tricalcium phosphate; and fluorapatite, and such osteoinductive substances as: bone morphogenetic proteins (e.g., rhBMP-2); demineralized bone matrix; transforming growth factors (e.g., TGF-β); osteoblast cells, and various other organic species known to induce bone formation. Osteoinductive materials such as BMP may be applied to articles of the invention, for example, by immersing the article in an aqueous solution of this material in a dilute suspension of type I collagen. Osteoinductive materials such as TGF-β may be applied to an article of the invention from a saline solution containing an effective concentration of TGF-β.

The continuous supporting framework having interconnecting interstices or openings may be considered to be the primary load bearing element, and the osteoconductive material commonly is much weaker than the supporting framework. The supporting framework is preferably formed, as mentioned above, of a ceramic material such as zirconia. The framework structure is formed such that the interstices or openings themselves, on average, are wider than are the thicknesses of the struts which separate neighboring interstices. The load bearing framework is essentially completely continuous and self interconnected in three dimensions, and the void portion is also essentially completely continuous and self interconnected in three dimensions. These two three dimensionally interconnected parts are intercolated with one another. This can be referred to as a 3—3 connectivity structure where the first number refers to the number of dimensions in which the load bearing framework is connected, and the second number refers to the number of dimensions in which the void portion is connected. The concept of connectivity is explained at greater length in Newnham et al. "Connectivity and Piezoelectric-Pyroelectric Composites," Materials Research Bulletin, Vol. 13 pp. 525–536 (1978), the teachings of which are incorporated herein by reference. With the supporting framework described herein, the framework itself is given a 3 as it is connected in 3 dimensions, and the void portion is treated likewise. In contrast, partially sintered assemblages of powders invariably contain isolated pores or voids which are not connected to all other voids. A material with all isolated (that is, dead end) pores in a dense matrix would have 3-0 connectivity. A material having pores that pass completely through the matrix in one dimension would yield 3-1 connectivity, and a material having pores that interconnect two perpendicular faces but not the third would have 3-2 connectivity.

The opening sizes in the supportive framework preferably are at least about 50 μm and preferably are on the order of 200 μm to about 600 μm. It is preferred that there be substantially no pores or voids less than 50 μm. It should be understood that the openings in the supportive framework are of myriad irregular shapes. The interconnected openings or interstices through which biological ingrowth processes can take place define in three dimensions a labyrinth in which bone ingrowth and vascularization can occur; that is, the openings have many junctures with other openings to thus define tortuous pathways through the framework. In general, it is believed that in order to adequately support the growth of bone into the framework openings, the openings must be capable of accommodating the passage of tissue having transverse dimensions of at least about 50 μm. Conceptually, it is convenient to think of a 50 μm opening in materials of the invention as being capable of accommodating the passage through it of a "worm" having a round cross section and a transverse diameter of 50 μm. Put another way, a 50 μm opening should enable passage through it of a sphere having a 50 μm diameter. Although there is no completely satisfactory way known to us for measuring the opening sizes, it is possible to examine a scanning electron micrograph of a cross section of an article of the invention and viewing it as a planar projection of the structure, drawing several lines across the micrograph, measuring the openings that intersected by the lines, and using averaging and standard deviation techniques to permit the size of the openings to be assessed An important feature of articles of the invention is that the interstices of the article remain at least partially open even with the presence of the osteoconductive and/or osteoinductive material. "Open", in this sense, means that the interstices are not plugged and that a fluid may pass entirely through the article from one side to the other.

Zirconia and other ceramics, when used to form the supportive framework, are exceedingly hard and are far more rigid than is bone. Although it would be desirable to employ as the supportive framework a material having a modulus of elasticity nearer to that of bone, bone substitute materials of the invention employing rigid materials having quite open interstices work well. It is believed that the ultimate union of bone with such porous articles during the healing process occurs over a large surface area and depth as the encroaching bone penetrates deeply into the interstices of the article. The substantial bone/ceramic interface that results enables forces to be readily transmitted to and from the ceramic framework with significantly less stress concentration in comparison to structure resulting from a bone/ceramic union that occurs within a small area of surface-to-surface contact and with little or no penetration of bone into the article.

When the osteoconductive material utilized is a ceramic, e.g., a calcium phosphate such as hydroxyapatite, for example, and the supportive framework is a ceramic such as zirconia, several methods may be employed in the manufacture of the article of the invention. The supportive zirconia framework structure can be fabricated as indicated above, by coating a slip of zirconia on the surface of the struts of a reticulated organic material such as a foam of polyurethane, polyester, polyether or the like, and subsequently raising the temperature of the coated foam to drive off slip solvent, to pyrolize or burn off the organic foam material, and finally to heat the ceramic to cause the ceramic particles to at least partially sinter.

Once the ceramic framework has cooled, its struts may be coated with a slip containing a calcium phosphate (e.g., hydroxyapatite), the latter material forming a coating upon the framework material with excess slip draining from the framework structure. As pure calcium phosphate does not bond well to pure zirconia, it may be desirable to provide intervening layers which contain a fraction of both materials. The resulting material may again be heated to drive off the slip solvent and, if desired, to sinter the hydroxyapatite material to cause particles thereof to at least partially fuse to one another. In this configuration the resulting interstices of the supportive framework are open from one surface to the other, and the interstices of the second osteoconductive material are continuous, interconnect with one another, and interconnect with (and are coextensive with) the interstices of the supportive framework component.

In forming the article, it may be desirable to heat the zirconia framework component to a temperature at which the slip solvent has substantially all been driven off and partial sintering has begun, this condition being referred to as a partially sintered stage. At this point, a hydroxyapatite slip or composite zirconia and hydroxyapatite slip may be applied, the slip solvent driven off with heat, and the zirconia and hydroxyapatite are raised to a sintering temperature and sintered together.

In a modification of this embodiment described above, the slip of hydroxy appetite may have added to it viscosity control agents and a foaming agent such as hydrogen peroxide, or compressed gas. Upon introduction into the supportive zirconia framework structure of the hydroxyapatite slip, heating causes the slip to bubble and foam such that a number of smaller pores are formed in the hydroxyapatite matrix with the pores of the hydroxyapatite material nonetheless remaining substantially interconnected, continuous, and interconnecting with pores of the zirconia framework In another embodiment, the slip used to coat the polymeric foam and produce the reticulum contains fractions of both the supportive framework material (such as zirconia) and the osteoconductive material (such as hydroxyapatite.) The reticulated polymeric substrate is coated with slip and the excess is allowed to drain. Further excess slip is removed by passing the article through squeeze rollers or by impacting the article with compressed air. The resulting material is heated to drive off solvent, to pyrolyze the organic constituents, and to co-sinter the two components of the composite. In the zirconia-hydroxyapatite system, the osteoconductive material is preferably included in a range of up to about 50 volume percent and more preferably about 10 to 25 volume percent with respect to the total zirconia/hydroxyapatite volume, sufficient osteoconductive material being used so as to provide an osteoconductive surface with respect to growing bone. Appropriate structures may use, for example, 25 volume per cent of hydroxyapatite and 75% of YSZ (yttria-stabilized zirconia). The reticulated article that results has struts which are comprised of an intimate mixture of the two materials. The hydroxyapatite may appear as very small islands on the surface of the zirconia strut. In any event, in this embodiment, the osteoconductive material remains exposed to the openings in the article so as to provide an osteoconductive affect with respect to encroaching bone.

When the framework component is of metal, the two-part system with interconnected pores can be formed in the same manner as when the framework component is of ceramic materials, that is, the osteoconductive material may be incorporated within the struts or may be coated upon the walls of the metal struts, or foamed within the interstices and sintered.

The bone substitute materials of the invention can be formed into the appropriate configurations for use as a bone substitute by several methods. In one preferred method, an organic material with open interstices such as a reticulated polyurethane foam is simply cut using ordinary cutting instruments such as scissors, scalpels, hot wire cutters and the like until it has the configuration desired. The thus configured foam material is used in any of the foregoing methods to produce the article of the invention. In another method, an organic foam such as that referred to earlier is coated with a zirconia or other ceramic slip and is heated to drive off solvent and convert the ceramic to the "green" state, at which point it can be shaped into the desired configuration. In a further method, a bone substitute of the invention which has been fully sintered can be shaped by standard machining methods such as sawing and grinding, water jet or laser cutting, etc.

If the supporting framework of the article is of metal, it can be shaped through appropriate machining to the desired form before introducing an osteoconductive or osteoinductive material. It is contemplated that the pores of a metal material may be first filled with wax and the resulting structure frozen so that the wax supports the metal structure during machining, following which the wax is simply melted to enable the wax to escape. This procedure may have utility particularly when the metal framework component comprises a very thin walled structure with large void openings, the struts of which, accordingly, can be unintentionally easily bent.

In a further embodiment, articles of the invention comprise a supporting framework with added resilient materials, the framework itself having relatively large openings and a high void volume and being attached, as by sintering to a second, denser structural element which may be of the same or different material but which has smaller openings and a smaller void volume. Preferably, this denser portion is substantially fully dense, that is, it has a void volume less than 10%. The denser portion may take the form a semitubular plate, a rod useful as a stem receivable in the intramedullary canal of a long bone for a total hip or knee replacement, or a plate useful as a tibial tray of a knee prosthesis, etc. The latter material may be formed as a rod or stem, as may be useful for femoral hip stem prostheses or tibial tray prostheses, or may be formed as a thin layer relative to the first portion so that the resulting structure mimics natural bone in that the second portion may resemble cortical bone—the hard, dense, outer layer of a bone—whereas the first portion may be somewhat more open and porous and hence more closely resembles cancellous bone.

FIG. 4 shows a femoral hip stem prosthesis 30 made entirely of ceramic, the prosthesis having a dense stem portion 32, an angular neck 34 terminating in an articulating ball 36, and an angular shoulder portion 38. As shown in FIG. 4, the shoulder portion includes a thick layer 40 of an article of the invention having a framework with relatively large openings, carried by the denser portion 42 of the prosthesis. The coating 38 promotes bone ingrowth when the prosthesis has been implanted in the femur of a patent.

Figure 5:
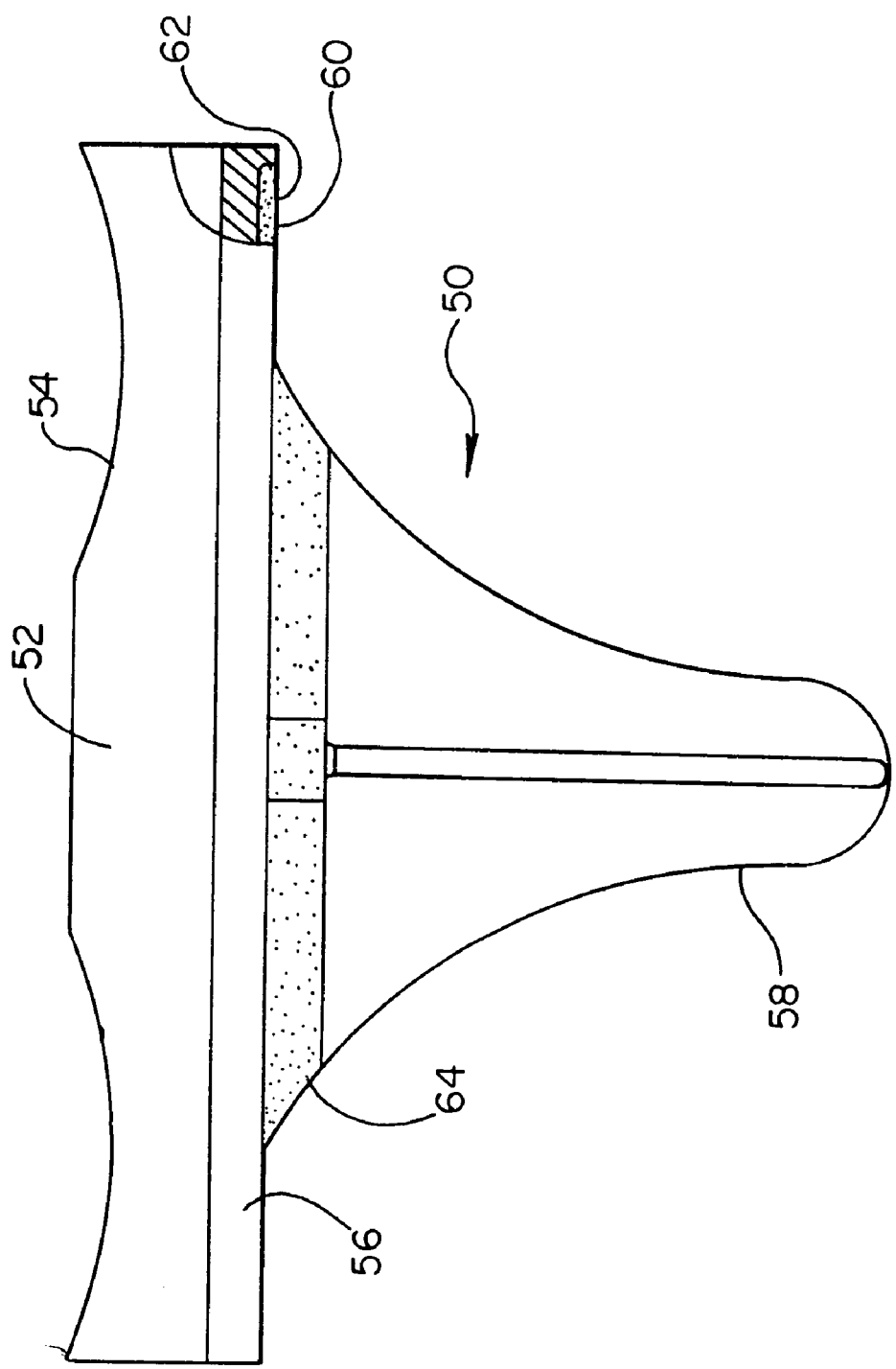
FIG. 5 is a broken away view of a tibial tray prosthesis utilizing an embodiment of the invention.

FIG. 5 depicts a tibial tray 50 having an upper plate 52 of ultra high molecular weight polyethylene having an articulating upper surface 54. The ultra high molecular weight polyethylene plate is supported by a plate 56 of the dense material of the invention, the plate 56 being integrally formed with a downwardly extending stem 58. The open framework material of the invention is shown in the form of a plate 60 which is received within a downwardly open recess 62 formed in the bottom of the plate 56, the framework 60 extending downwardly about the upper end of the stem, as shown at 64 in a relatively thick layer to promote bone ingrowth in this area.

The dense portion of the above described constructs can be prepared by any of the common ceramic forming techniques such as slip casting, tape casting, or coating and drying successive layers of slip onto a surface of a "foam" until a dense layer is formed. Dry pressing, injection molding and extrusion techniques may also be appropriate. The "green" dense portion is joined to the "green" low density portion through the use of a ceramic slip of substantially similar composition to the slip used in the formation of the low density portion or of a substantially similar composition to the slip used in the formation of the dense portion in the case of slip cast dense portion. "Green" here refers to the state of a ceramic article which has been formed and dried to a self-supporting structure but from which the organic constituents have not yet been removed. The dense portion may be alternatively comprised of a resorbable polymeric material, a resorbable ceramic material, or a resorbable composite material in addition to materials enumerated above.

During a surgical procedure, the openings of the articles of the invention may be filled with a calcium phosphate cement, to adhere the articles to bone, for example. The calcium phosphate cement hardens within the interstices and provides a secure bond to the articles.

The invention may be more easily understood by reference to the following non-limiting examples:

EXAMPLE 1

A zirconia slip was prepared by combining the following ingredients and mixing them thoroughly by ball milling in a polyethylene container using zirconia media:

150 grams partially stabilized zirconia powder (Zirconia Sales America)

2.25 grams dispersant (Rohm and Haas, product D-3021)

15 grams binder (Rohm and Haas product designation B-1000)

0.375 grams surfactant/wetting agent (Air Products Surfynol™ TG)

0.26 grams anti-foaming agent (Henkel Nopco™ NXZ)

36 ml deionized water

Pieces of reticulated polyester-polyurethane foam 10–80 pores per inch (Stephenson and Lawyer) were immersed in the above slip and repeatedly compressed to remove air bubbles trapped inside. The foams were removed from the slip and the excess slip was allowed to drain. Further excess slip was removed by passing the foams between a pair of stainless steel squeeze rollers several times. The resulting pieces were allowed to dry at room temperature followed by drying at temperatures up to 100° C. in air. When the pieces appeared dry, they were heated to pyrolyze and remove organics (binder, dispersant, surfactant, anti-foam agent, and reticulated polymer foam) and then were sintered at a temperature of about 1400° C. for one hour. The preferred thermal cycle for the above involves raising the temperature of the pieces at the rate of 2° C. per minute to 600° C., holding the temperature at 600° C. for two hours, and then raising the temperature at the rate of 5° C. per minute to 1400° C., with a one hour hold at this temperature. The furnace is then cooled to room temperature at a rate of about 10° C. per minute.

The resulting product was a strong, light weight, porous zirconia framework or reticulum of zirconia having a void volume of about 76%. The framework was then coated with a slip containing both zirconia and hydroxyapatite. The slip was prepared by combining and ball milling, as described above, the following ingredients:

75 g partially stabilized zirconia (Zirconia Sales America)

12.89 g hydroxyapatite (Plasma Biotal)

1.5 g D-3021 dispersant 10 g B-1000 binder 0.25 g Surfynol™ TG surfactant/wetting agent 0.24 g Nopco NXZ anti-foaming agent 32 ml deionized water The hydroxyapatite provided 25% by volume of the combined hydroxyapatite and zirconia.

Pieces of the zirconia prepared as described above were immersed in the slip and mechanically agitated to remove air bubbles and to assure complete penetration of the slip into the openings. Excess slip was allowed to drain, and further slip was removed with a stream of compressed air. The pieces were dried and were then raised at the rate of 5° C. per minute to a sintering temperature of 1400° C. and were held at this temperature for one hour. The resulting product comprises a strong ceramic framework of zirconia, the struts of which have a surface layer comprised of 75 volume percent zirconia and 25 volume percent hydroxyapatite. The structure of this product is illustrated in FIG. 1, and note may be made of the open nature of the supporting zirconia supporting framework and the 3,3-connectivity of the framework and the hydroxyapatite.

If desired, an additional layer or layers may be added to the above structure. For example, in one embodiment, specimens of the above structure were immersed in a slip containing approximately 50% by volume of zirconia and hydroxyapatite, the specimens being drained, dried, and sintered as above at 1400° C.

EXAMPLE 2

This example describes the preparation of a zirconia-hydroxyapatite composite supporting framework, the struts of which bear a coating of hydroxyapatite.

Two ceramic slips were prepared. The first, comprising zirconia containing 15 volume percent hydroxyapatite and referred to as a ZHA-15 slip, was prepared by ball milling as in Example 1 using the following ingredients:

273.99 g partially stabilized zirconia 26.01 g hydroxyapatite (HiMed)

3 g poly(ethylene oxide) binder (Acros)

6 g dispersant (Darvan™ C, R.T. Vanderbilt)

0.75 g Surfynol™ TG surfactant/wetting agent 126 ml deionized water

The second slip, referred to as an HA slip, was prepared by ball milling using the following ingredients:

50 g hydroxyapatite (HiMed)

0.5 g poly(ethylene oxide) binder (Acros)

0.125 g Surfynolm TG surfactant/wetting agent 1 g dispersant (Darvan™ C, R.T. Vanderbilt)

76 ml deionized water

Specimens of the reticulated polyester-polyurethane foam referred to in Example 1 were coated as in Example 1 with the ZHA-15 slip. The coated specimens were dried to the "green" state and then heat treated as in Example 1 to remove organic materials and were sintered at 1400° C.

Depending upon the relative amounts of zirconia and hydroxyapatite that are used, the hydroxyapatite may appear as small "islands" on the surface of the struts; this is illustrated in FIG. 3. Sufficient hydroxyapatite or other osteoconductive material is employed so provide the surface of the struts with osteoconductive properties.

Following cooling, the specimens were coated with the HA slip, dried, heated to remove organic materials, and were sintered at 1400° C. The struts of the resulting structure were comprised of a core of partially stabilized zirconia composite with 15 volume percent hydroxyapatite and a surface layer of hydroxyapatite.

EXAMPLE 3

An "exoskeletal" structure was prepared consisting of an open pore structure as described above bonded to a dense support "plate" comprised of zirconia in one embodiment and ZHA-15 in another embodiment, the open pore structure simulating cancellous bone and the dense structure simulating cortical bone.

Support plates of zirconia and ZHA-15 were slip cast onto flat plaster of paris surfaces utilizing the zirconia slip of Example 1 and the ZHA-15 slip of Example 2, respectively. Green reticulated structures of ZHA-15 as prepared in Example 2 were placed into the wet slip of each embodiment immediately after the latter were cast. The resulting specimens were dried and heated, and the plate portions were trimmed when they reached the "leather hard" stage. Drying was done in air followed by drying in an oven at temperatures up to 100° C. The specimens were further heated to remove organic materials, and each was sintered as a unit at 1400° C. Following cooling, the porous portion of each specimen that simulated cancellous bone was recoated with the ZHA-15 slip. Excess slip was removed by compressed air, and the specimens were again dried and sintered at 1400° C. for 1 hour. The resulting specimens each exhibited a highly porous portion mimicking cancellous bone that was securely bonded to a more dense plate portion mimicking cortical bone, and is illustrated in FIG. 4.

EXAMPLE 4

An hydroxyapatite-containing suspension was prepared by combining and mixing:

20 g hydroxyapatite 18 ml of an aqueous solution containing 1% of a foam stabilizer (Lattice™ NTC, FMC Corp.)

18 ml 3% hydrogen peroxide solution

Specimens of zirconia were prepared and sintered as in Example 1, forming an endoskeletal framework, and the framework openings were filled with the hydroxyapatite suspension. The specimens were heated at the rate of 10° C. per hour to a temperature of 80° C. and were held at this temperature for 2 hours. Heating of the suspension causes the hydrogen peroxide to decompose and release oxygen gas bubbles. These bubbles cause the suspension to foam and rise. Upon further heating, the hydroxyapatite foamed structure stabilizes. The specimens were further heated to remove organic materials and was sintered at 1300° C. for one hour. The resulting structure is illustrated in FIG. 2, and comprises a zirconia framework having openings partially filled with a highly porous (approximately 50 volume percent pore space) hydroxyapatite foam. The interstices or openings of the zirconia framework remain open and unplugged, as shown, and the openings of the zirconia framework communicate with the pores of the foamed hydroxyapatite coating.

While a preferred embodiment of the present invention has been described, it should be understood that various changes, adaptation and modification may be made therein without departing from the spirit of the invention and the scope of the appended claims.

What is claimed is:

1. A strong, porous article useful as a bone substitute material and having an outer surface defining a shape having a bulk volume, the article comprising a continuous strong supportive sintered, load-bearing framework having struts defining a plurality of interconnecting interstices throughout the bulk volume, and a porous osteoconductive composition carried by said supporting framework, said article having interconnecting openings extending throughout said volume and opening through said surface with said osteoconductive composition being exposed to said interconnected openings.

2. The article of claim 1 wherein said osteoconductive composition extends throughout said bulk volume.

3. The article of claim 1 wherein interconnecting interstices of said supportive framework terminate in said outer surface and wherein the osteoconductive composition extends from said outer surface inwardly of said shape but not throughout the entire bulk volume of the shape.

4. The article of claim 1 wherein said osteoconductive composition is carried as a continuous coating on said struts.

5. The article of claim 1 wherein said osteoconductive composition includes pores that communicate with but are not coextensive with interstices of the supportive framework.

6. The article of claim 1 wherein said supportive framework has a void volume that is at least 50% of the bulk volume of the article.

7. The article of claim 1 wherein said supportive framework includes said osteoconductive composition incorporated in said struts.

8. The article of claim 1 including in said openings a calcium phosphate bone cement.

9. The article of any one of claims 1 through 6 including a comparatively dense structural element attached to a surface of said bulk volume and having a porosity not greater than 10%.

10. The article of claim 9 wherein said structural element comprises a rod useful as a stem receivable in the intramedullary canal of a long bone.

11. The article of claim 9 wherein said structural element comprises a plate useful as the tibial tray of a knee prosthesis.

12. The article of any one of claims 1 through 8 wherein said supportive framework is ceramic.

13. The article of any one of claims 1 through 8 including an osteoinductive material carried by said structure and exposed to said interstices.

14. A strong, porous article useful as a bone substitute material and having an outer surface defining a shape having a bulk volume, the article comprising a continuous strong supportive sintered, load-bearing framework comprising zirconia, the framework having struts defining a plurality of interconnecting interstices throughout the bulk volume, and a porous osteoconductive composition carried by said supporting framework, said article having interconnecting openings extending throughout said volume and opening through said surface with said osteoconductive composition being exposed to said interconnecting openings.

15. The article of claim 14 wherein said supporting framework includes a ceramic osteoconductive composition carried at discrete locations along said struts and exposed to said interconnecting openings.

16. The article of claim 14 wherein said osteoconductive composition is carried as a substantially continuous coating formed on said struts, and wherein said supporting framework and said osteoconductive composition have 3—3 connectivity.

17. The article of claim 15 or claim 16 wherein said ceramic osteoconductive composition comprises a calcium phosphate compound.

18. A strong, porous article useful as a bone substitute material and having an outer surface defining a shape having a bulk volume and having interconnecting openings extending throughout said volume and opening through said surface, the article comprising a continuous strong supportive sintered, load-bearing framework having struts defining a plurality of interconnecting interstices throughout the bulk volume, a first porous osteoconductive composition carried by said supporting framework, and a second porous osteoconductive composition carried by said first porous osteoconductive composition and exposed to said interconnected openings.

19. The article of claim 18 wherein said first and second porous osteoconductive compositions each include an osteoconductive material with the concentration of osteoconductive material in the second composition being greater than that of the first composition.

20. A strong, porous article useful as a bone substitute material and having an outer surface defining a shape having a bulk volume and having interconnecting openings extending throughout said volume and opening through said surface, the article comprising a continuous strong supportive sintered, load-bearing framework comprising zirconia, the struts defining a plurality of interconnecting interstices throughout the bulk volume, a first porous osteoconductive composition including hydroxy appetite carried by the supportive framework, and a second porous osteoconductive composition carried by said first composition and exposed to said interconnecting openings, said second composition containing hydroxy appetite in a concentration greater than that of the first composition.

21. The composition of claim 20 wherein said first and second porous osteoconductive compositions include zirconia.

* * * * *